United States Patent
Ko et al.

(10) Patent No.: US 10,249,473 B2
(45) Date of Patent: Apr. 2, 2019

(54) TRANSPORTING APPARATUS AND METHOD OF TRANSPORTING USING THE SAME

(71) Applicant: SAMSUNG ELECTRONICS CO., LTD., Suwon-si (KR)

(72) Inventors: Wonhee Ko, Seoul (KR); Insu Jeon, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 136 days.

(21) Appl. No.: 14/848,723

(22) Filed: Sep. 9, 2015

(65) Prior Publication Data

US 2016/0114986 A1    Apr. 28, 2016

(30) Foreign Application Priority Data

Oct. 23, 2014    (KR) .......................... 10-2014-0144289

(51) Int. Cl.

| B65G 47/74 | (2006.01) |
| B65G 65/00 | (2006.01) |
| H01J 37/16 | (2006.01) |
| G01R 19/00 | (2006.01) |
| H01J 37/20 | (2006.01) |
| H01J 37/18 | (2006.01) |

(Continued)

(52) U.S. Cl.
CPC .......... *H01J 37/16* (2013.01); *G01R 19/0084* (2013.01); *H01J 37/185* (2013.01); *G01N 1/42* (2013.01); *G01N 2001/002* (2013.01); *H01J 2237/202* (2013.01); *H01J 2237/204* (2013.01)

(58) Field of Classification Search
CPC .............. G01N 1/42; G01N 2001/002; G01R 19/0084; H01J 2237/202; H01J 2237/204; H01J 37/16; H01J 37/185
USPC .......................................................... 269/27
See application file for complete search history.

(56) References Cited

U.S. PATENT DOCUMENTS 4,292,727 A * 10/1981 Maxner .............. H05K 13/0473
                                                              140/105
4,574,462 A    3/1986 Jackson
(Continued)

FOREIGN PATENT DOCUMENTS

EP    0161856 A2 *  11/1985  .............. G01N 1/42
JP    3030546 U      11/1996
(Continued)

OTHER PUBLICATIONS

McAllister Technical Services; "ZA-series Instructions", Manufacturers of surface analytical instruments and devices, Aug. 2012, Total 10 pages.
(Continued)

*Primary Examiner* — Marc Carlson
(74) *Attorney, Agent, or Firm* — Sughrue Mion, PLLC

(57) ABSTRACT

A transporting apparatus configured to transport an object to a storage container includes: a transporting rod having one end configured to connect to the object, the transporting rod extending in a transporting direction of the object; a transporting portion that moves the transporting rod in the transporting direction of the object; and a contact sensor portion provided on an outer wall of the transporting rod and configured to sense contact between the transporting rod and the storage container.

12 Claims, 9 Drawing Sheets

(51) Int. Cl.
   *G01N 1/00*   (2006.01)
   *G01N 1/42*   (2006.01)

(56) References Cited

U.S. PATENT DOCUMENTS

| | | | | | |
|---|---|---|---|---|---|
| 4,580,416 | A * | 4/1986 | Sitte | ................ | G01N 1/42 62/383 |
| 4,745,764 | A * | 5/1988 | Sitte | ................ | G01N 1/42 62/51.1 |
| 4,745,771 | A * | 5/1988 | Linner | ................ | G01N 1/42 118/50.1 |
| 4,751,828 | A * | 6/1988 | Coulter | ................ | G01N 1/42 62/51.1 |
| 5,044,165 | A * | 9/1991 | Linner | ................ | B01D 8/00 118/50.1 |
| 5,165,165 | A * | 11/1992 | Aoki | ................ | H05K 13/0404 140/105 |
| 5,226,632 | A * | 7/1993 | Tepman | ................ | F16K 1/10 137/315.27 |
| 6,158,945 | A * | 12/2000 | Anderson | ................ | B65F 3/041 414/408 |
| 6,312,209 | B1 * | 11/2001 | Duell | ................ | B65F 3/046 414/408 |
| 7,384,128 | B2 * | 6/2008 | Sheahan | ................ | B41J 2/0451 347/40 |
| 7,637,039 | B2 * | 12/2009 | Toda | ................ | E02F 9/2235 37/195 |
| 8,475,739 | B2 * | 7/2013 | Holmes | ................ | B01L 3/0217 422/500 |
| 8,639,404 | B2 * | 1/2014 | Sugiyama | ................ | B60K 6/12 701/22 |
| 9,304,067 | B2 * | 4/2016 | Hayworth | ................ | G01N 1/06 |
| 2008/0041069 | A1 * | 2/2008 | Vicar | ................ | G01N 1/06 62/51.1 |
| 2008/0105524 | A1 * | 5/2008 | Olszewski | ................ | H01H 1/0015 200/312 |
| 2010/0294046 | A1 * | 11/2010 | Boeke | ................ | C12M 33/07 73/863.01 |
| 2014/0167342 | A1 * | 6/2014 | Jin | ................ | B23P 21/00 269/27 |
| 2015/0023475 | A1 * | 1/2015 | Gordon | ................ | A61B 6/4405 378/195 |
| 2016/0225219 | A1 * | 8/2016 | Menon | ................ | G07F 11/04 |
| 2016/0229559 | A1 * | 8/2016 | Potters | ................ | B64F 1/368 |
| 2017/0205436 | A1 * | 7/2017 | Oonuma | ................ | G01N 35/025 |

FOREIGN PATENT DOCUMENTS

| | | |
|---|---|---|
| JP | 201181946 A | 4/2011 |
| KR | 100631748 B1 | 10/2006 |
| KR | 101388509 B1 | 4/2014 |

OTHER PUBLICATIONS

"MPPRL Series—Rotary and Linear Motion", UHV Design, p. 49 (total 1 page).

* cited by examiner

TRANSPORTING APPARATUS AND METHOD OF TRANSPORTING USING THE SAME

CROSS-REFERENCE TO RELATED APPLICATION

This application claims priority to Korean Patent Application No. 10-2014-0144289, filed on Oct. 23, 2014, in the Korean Intellectual Property Office, the disclosure of which is incorporated herein in its entirety by reference.

BACKGROUND

1. Field

The exemplary embodiments consistent with the present disclosure relate to transporting apparatuses and methods of transporting using the same.

2. Description of the Related Art

Recently, the necessity for transporting samples and components in a sealed space, such as a vacuum chamber or a low temperature container, is increasing in research related to semiconductor fabrication process devices, low temperature operating devices, and medical science and biology fields.

For example, in a transmission electron microscope (TEM) that uses electronic rays and electronic lenses, instead of a light source and light source lenses, cryogenic (CRYO) analysis using a CRYO-plunger for rapidly cooling a sample grid at a liquid nitrogen temperature (−196° C.) can be used to fix a biological specimen to be observed. In this case, since a cryogenic storage container used in CRYO analysis is maintained in a sealed state, a user cannot see the inside of the sealed storage container from the outside by the naked eye. Thus, when a sample or specimen is transported to the inside of the sealed storage container, the user cannot check for problems that may occur with the specimen or sample in the storage container.

SUMMARY

One or more exemplary embodiments may provide transporting apparatuses and methods of transporting using the same, which may enable a user to transport an object to the inside of a sealed storage container from the outside by the naked eye.

Additional aspects will be set forth in part in the description which follows and, in part, will be apparent from the description, or may be learned by practice of the presented exemplary embodiments.

According to an aspect of an exemplary embodiment, there is provided a transporting apparatus configured to transport an object to a storage container, the transporting apparatus including: a transporting rod having one end configured to connect to the object, the transporting rod extending in a transporting direction of the object; a transporting portion that moves the transporting rod in the transporting direction of the object; and a contact sensor provided on an outer wall of the transporting rod and configured to sense contact between the transporting rod and the storage container.

The transporting apparatus may be configured to transport the object to the storage container which may be a sealed container, an inside of which cannot be seen from the outside by a user.

The transporting apparatus may be configured to transport the object to the storage container which may be used in a high temperature process, a cryogenic process, or a semiconductor fabrication process.

The contact sensor may be provided plurally, and the contact sensors may be provided along the outer wall of the transporting rod at intervals separated by a predetermined distance.

The contact sensor may be provided plurally, and the contact sensors may include: contact portions provided on the outer wall of the transporting rod at intervals separated by a predetermined distance; an input channel which is electrically connected to the contact portions and configured to detect first reference signals; and a receiving channel which is electrically connected to the contact portions and configured to detect second reference signals in which a change in voltage from the first reference signals occurs.

The transporting apparatus may further include ball plungers provided along the outer wall of the transporting rod at intervals separated by a predetermined distance and including balls provided in the ball plungers so that part of the balls is exposed to the outer wall of the transporting rod.

The ball plungers may be electrically connected to the contact sensors, and the contact portions of the contact sensors may be provided on the ball plungers.

The transporting apparatus may further include an insulation member provided between the balls disposed in the ball plungers and formed of an insulating material.

The transporting apparatus may be a sample plunger of a cryogenic scanning probe microscope.

The transporting apparatus may further include: a transfer holder provided on one end of the transporting rod and configured to grasp the object; and a transfer holder connector connecting the transfer holder to the one end of the transporting rod.

The transporting apparatus may further include: a receiving portion configured to receive signals detected by the contact sensor; and a display configured to display information indicating whether the transporting rod is in contact with the storage container according to the signals received by the receiving portion.

The transporting apparatus may further include: an input portion configured to receive driving signals to drive the transporting portion; and a controller configured to determine whether to drive the transporting portion according to the signals received by the receiving portion and the driving signals received by the input portion.

The transporting portion may include: a transporting member fixed to one end of the transporting rod and configured to move in the transporting direction of the object; and a guide member provided to face the transporting member and configured as a hollow type plate member configured to receive and guide the transporting rod.

The transporting apparatus may further include a bellows provided between the transporting member and the guide member.

According to an aspect of another exemplary embodiment, there is provided a method for transporting an object using a transporting apparatus including a contact sensor configured to sense contact between the transporting apparatus and a storage container, the method including: inputting a transporting position of the object to the transporting apparatus; transporting the object to the storage container using the transporting apparatus according to the input transporting position; detecting whether part of the transporting apparatus is in contact with the storage container, by using the contact sensor, and generating a detection signal based on the detecting; and controlling driving of the transporting apparatus according to the detection signal.

The method may further include: displaying the detection signal on a display; and inputting correction signals for driving the transporting apparatus according to the displayed signals.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
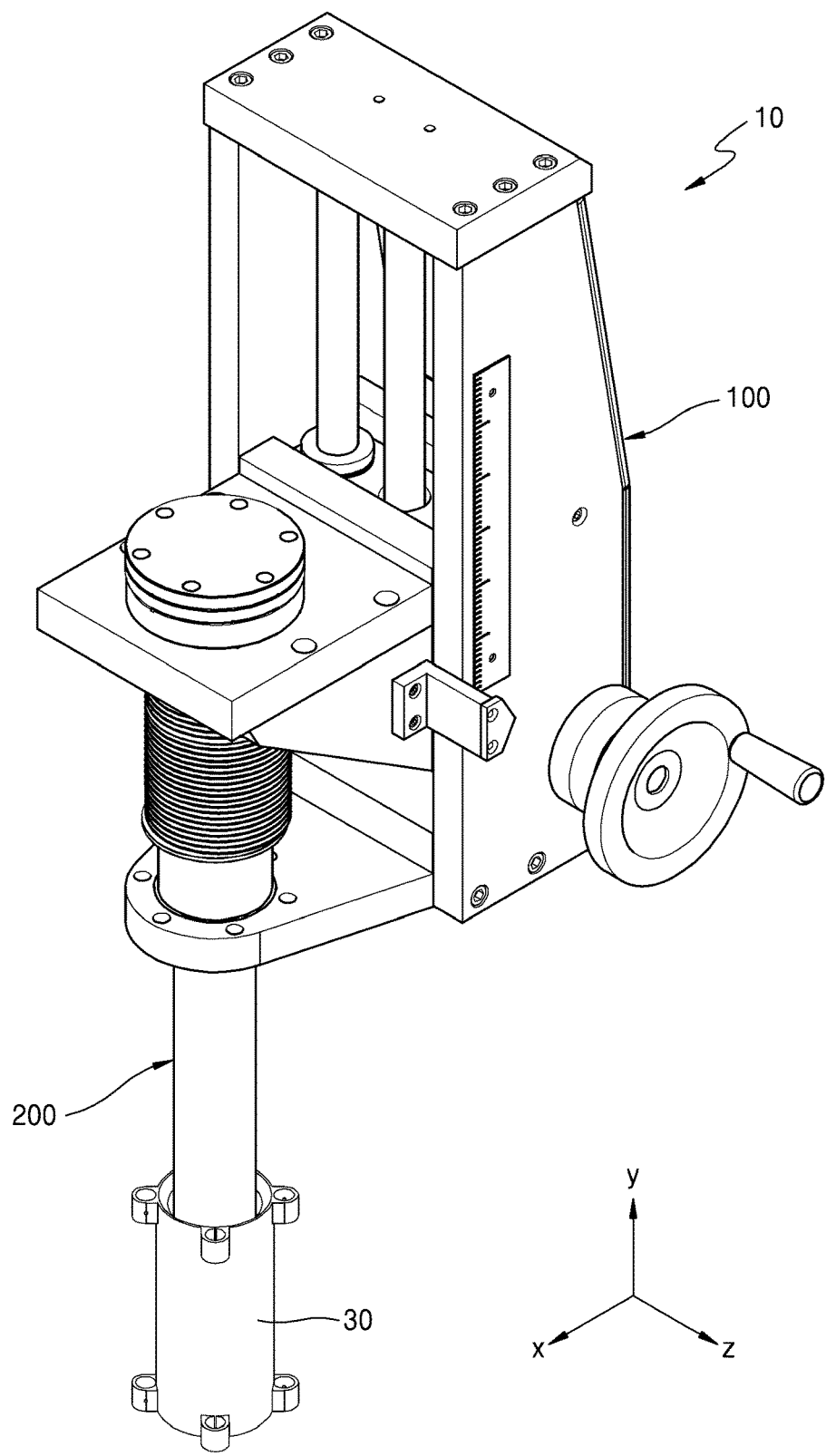
FIG. 1 is an assembling perspective view of a transporting apparatus and a storage container according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the exemplary embodiments. As used herein, the term "and/or" includes any and all combinations of one or more of the associated listed items.

Hereinafter, exemplary embodiments will be described below in more detail with reference to the accompanying drawings. Like reference numerals in the following drawings refer to like elements. In the drawings, sizes of elements may be exaggerated for clarity and convenience of explanation. The following exemplary embodiments are illustrative only, and various modifications of the exemplary embodiments are possible.

Hereinafter, it will be understood that when a layer, region, or component is referred to as being "formed on," another layer, region, or component, the layer, region or component can be directly or indirectly formed on the other layer, region, or component. That is, for example, intervening layers, regions, or components may be present.

It will be understood that although the terms "first", "second", etc., may be used herein to describe various components, these components should not be limited by these terms. These components are only used to distinguish one component from another.

As used herein, the singular forms "a," "an" and "the" are intended to include the plural forms as well, unless the context clearly indicates otherwise. It will be further understood that the terms "comprises" and/or "comprising" used herein specify the presence of stated features or components, but do not preclude the presence or addition of one or more other features or components.

Figure 2:
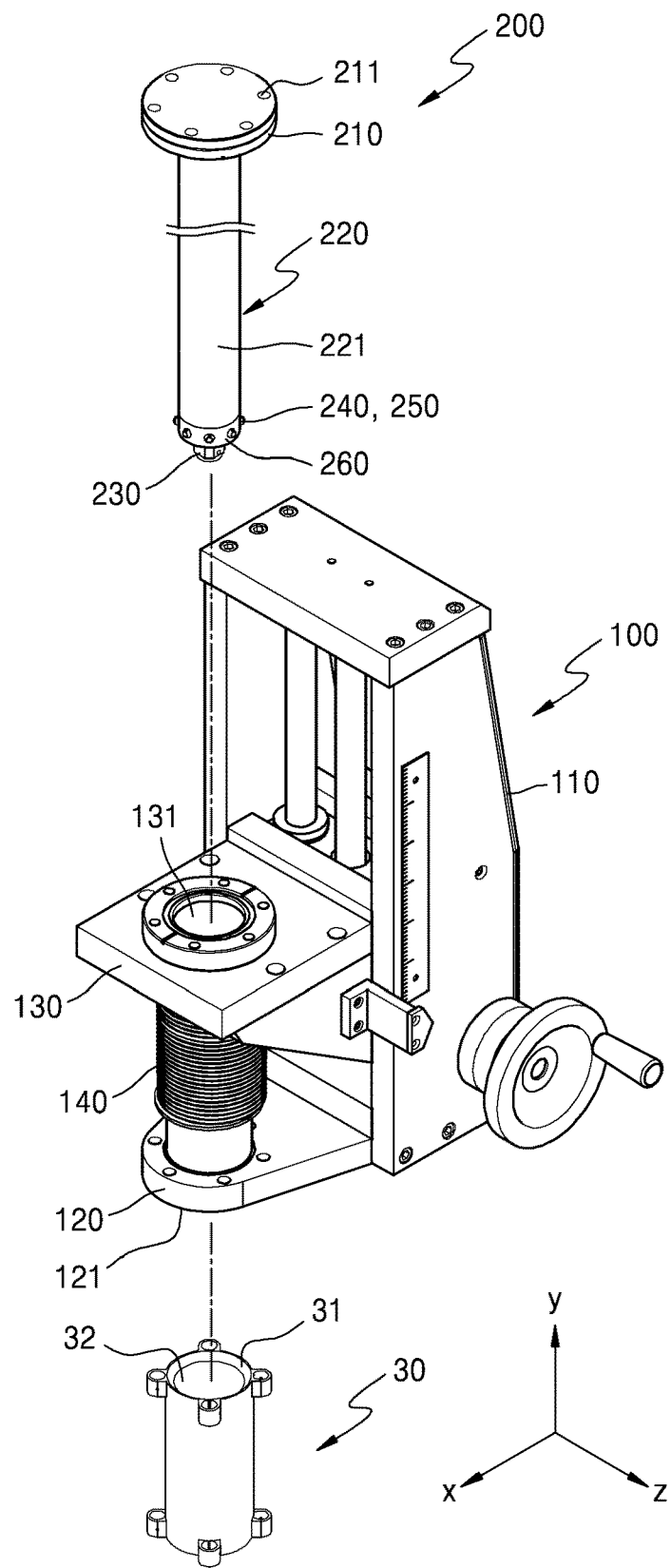
FIG. 2 is an exploded perspective view of the transporting apparatus illustrated in FIG. 1.
Figure 3:
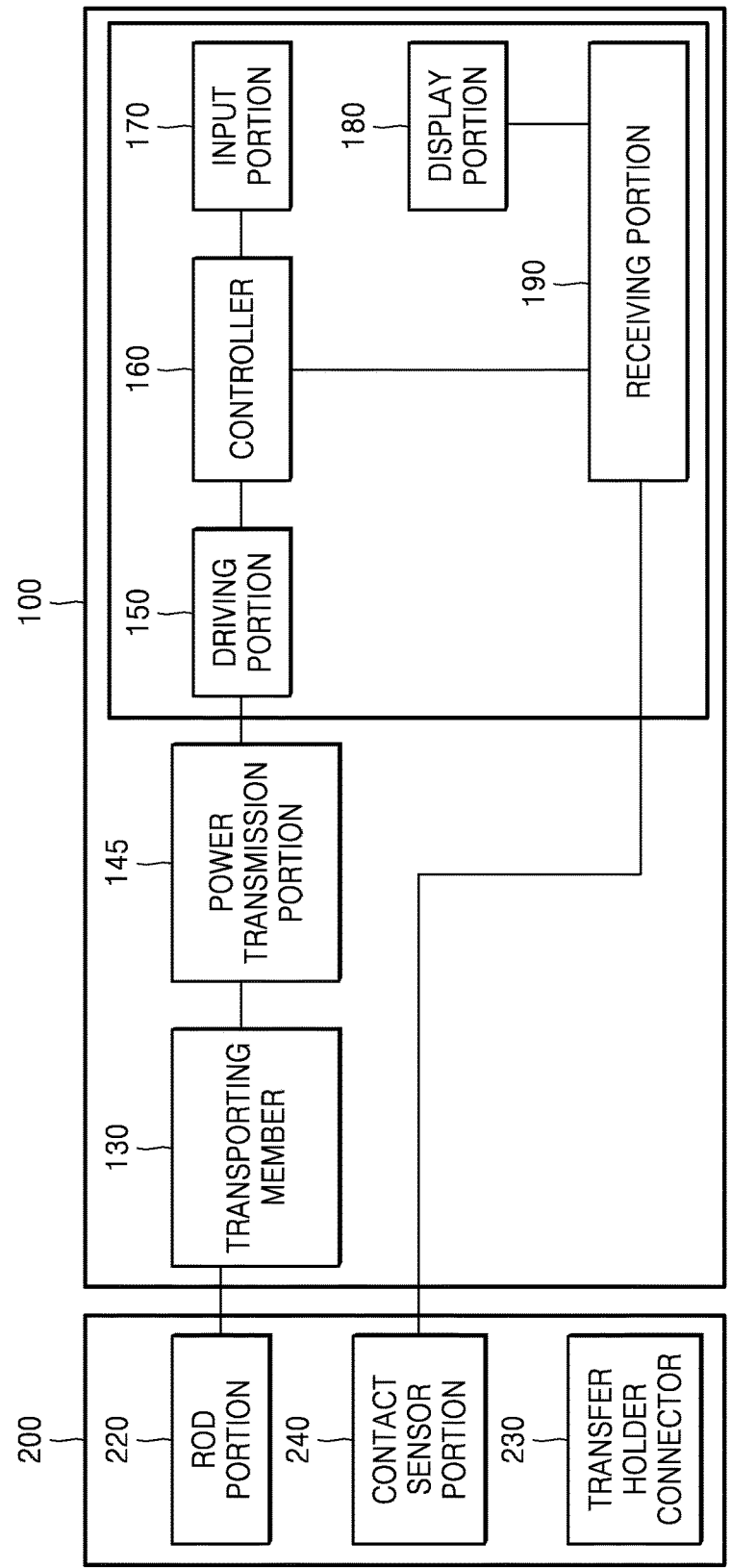
FIG. 3 is a block diagram of a schematic configuration of the transporting apparatus of FIG. 1.

FIG. 1 is an assembling perspective view of a transporting apparatus 10 and a storage container 30 according to an exemplary embodiment. FIG. 2 is an exploded perspective view of the transporting apparatus 10 illustrated in FIG. 1. FIG. 3 is a block diagram of a schematic configuration of the transporting apparatus 10 of FIG. 1.

The transporting apparatus 10 transports an object to be transported in a particular position. In an exemplary embodiment, the transporting apparatus 10 is implemented as a bellows transporter 10. However, the exemplary embodiments are not limited thereto. An arbitrary type of transporter that may transport the object to be transported in one axis direction, for example, a magnetic transporter, may also be implemented according to other exemplary embodiments. The object to be transported may be an arbitrary object that may be transported by a transporting rod 200 included in the transporting apparatus 10.

Referring to FIGS. 1 and 2, the transporting apparatus 10 may include a bellows transporting portion 100 and the transporting rod 200. The bellows transporting portion 100 according to an exemplary embodiment may include a main body portion 110, a guide member 120 fixed to the main body portion 110, a transporting member 130 that is movable in a y-axis direction, and a bellows 140 disposed between the guide member 120 and the transporting member 130.

The guide member 120 that is a hollow type plate member is disposed to be fixed to one side of the main body portion 110. A first opening 121, into which the transporting rod 200 may be inserted, may be formed in the center of the guide member 120. When the transporting rod 200 is moved in the y-axis direction, the guide member 120 may guide a movement direction of the transporting rod 200.

The transporting member 130 that is a hollow type plate member may be disposed to face the guide member 120 and may be moved in the y-axis direction by receiving power from a power transmission portion (see 145 of FIG. 3) disposed in the main body portion 110. A second opening 131, into which the transporting rod 200 may be inserted, may be formed in the center of the transporting member 130.

The bellows 140 that is a wrinkle member disposed between the guide member 120 and the transporting member 130 may be disposed so that one end of the bellows 140 may be fixed to a bottom end of the transporting member 130. When the guide member 120 and the transporting member 130 are spaced apart from each other by a predetermined distance or more, the bellows 140 may be maintained in an expanded state. When the transporting member 130 is moved and the guide member 120 and the transporting member 130 are spaced apart from each other by a predetermined distance or less, the bellows 140 may be compressed.

The transporting rod 200 is a transporting unit for transporting the object to be transported, which may be connected to one end of the transporting rod 200, to the storage container 30, and the transporting rod 200 may include a fixed portion 210, a rod portion 220, a transfer holder connector 230, and one or more contact sensor portions 240. The fixed portion 210 is a device for fixing the transporting rod 200 to the transporting portion 100 and may include a fastening unit 211 including a permanent magnet, a bolt and a nut. The transporting rod 200 may be fixed to an upper portion of the transporting member 130 using the fastening unit 211. Thus, the transporting rod 200 may be moved in the y-axis direction together with the transporting member 130.

The rod portion 220 is a connection member having the fixed portion 210 provided at one end thereof and the transfer holder connector 230 provided at another end thereof. The rod portion 220 may be disposed to be inserted into the first opening 121 of the guide member 120 and the second opening 131 of the transporting member 130 and may be moved in the y-axis direction according to movement of the transporting member 130. For example, the rod portion 220 is configured as a rectilinear rod member that extends in a transporting direction of the object to be transported. However, exemplary embodiments are not limited thereto. The rod portion 220 having various shapes including a curved shape may be formed according to a transporting path of the object to be transported.

A transfer holder 225 that may grasp the object to be transported, for example, a gripper or pincer, may be mounted on the transfer holder connector 230 that is a connection member disposed on one end of the rod portion 220.

The one or more contact sensor portions 240 are detection devices that may detect contact between the storage container 30 and the rod portion 220 that may occur when the rod portion 220 is moved in the storage container 30. The one or more contact sensor portions 240 may be disposed along an outer wall portion 221 of the rod portion 220. For example, the one or more contact sensor portions 240 may be implemented as a voltage detection type. However, exemplary embodiments are not limited thereto. A method of detecting contact between the storage container 30 and the rod portion 220 using the one or more contact sensor portions 240 will be described below with reference to FIGS. 4 and 5.

The storage container 30 is a device which may transport the object to be transported, and may be a storage device used in a semiconductor fabrication process or a cryogenic device which is maintained in a vacuum state, a high temperature state, or a cryogenic state and an inside of which may not be seen from the outside by a user's naked eye. For example, the storage container 30 may be a specimen storage device used in a cryogenic scanning probe microscope. In this case, the transporting apparatus 10 may be a sample plunger of the cryogenic scanning probe microscope. In the storage container 30 according to an exemplary embodiment, an opening 31 may be formed in an upper portion of the storage container 30. The rod portion 220, on which the object to be transported is mounted, may be inserted into the opening 31. An inner wall portion 32, having a cylindrical shape onto which the rod portion 220 may be moved, may be formed in the storage container 30.

Referring to FIG. 3, the body portion 110 may include a driving portion 150 that may transfer power to the power transmission portion 145, a controller 160 that may control the driving portion 150, an input portion 170 that may input signals to the controller 160, a receiving portion 190 that may receive signals detected by the contact sensor portions 240, and a display portion 180 that may display the signals received by the receiving portion 190.

The driving portion 150 may be a motor device that may transfer power to the power transmission portion 145. For example, the power transmission portion 145 may be configured as a hydraulic device. The driving portion 150 may transfer power to the transporting member 130 by applying transferring power to a hydraulic pump included in the hydraulic device and by applying a hydraulic pressure to a cylinder and a piston device included in the hydraulic device. Transferring power to the transporting member 130 using the hydraulic device is a well-known technology and thus, a detailed description thereof will be omitted.

The controller 160 may control the driving portion 150 according to the signals input to the input portion 170 and the receiving portion 190. Also, the controller 160 may process the result of detected signals received by the receiving portion 190 as an image signal so as to display the result of detected signals. The controller 160 may be implemented in the shape of one microprocessor module or in the shape of a combination of two or more microprocessor modules. That is, the implementation shape of the controller 160 is not limited to any particular configuration.

The input unit 170 is an input device configured to receive user commands for manipulating the transporting apparatus 10 and may include a button, a keypad, a switch, or a touch interface, for example.

The display portion 180 is a display device for displaying the result of detection of the position of the transporting rod 200 and contact between the transporting rod 200 and the storage container 30 and may be implemented as many different types of displays, for example a liquid crystal display (LCD) panel or an organic light emitting diode (OLED) panel.

Figure 4A:
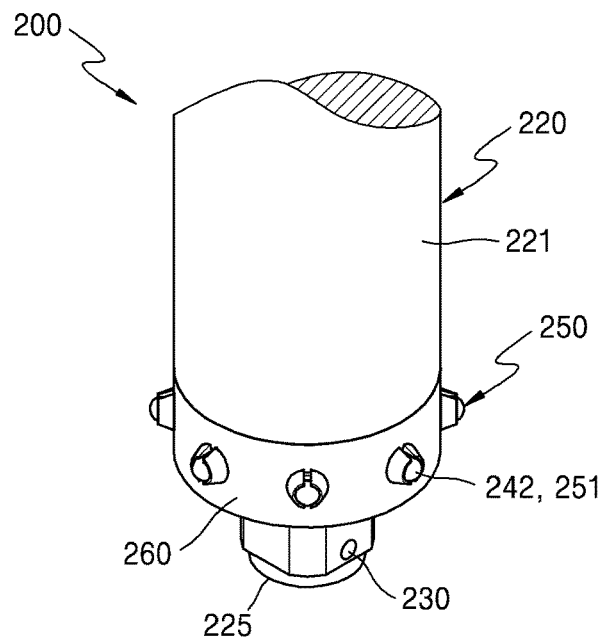
FIG. 4A is a partial perspective view of one end of a transporting rod.
Figure 4B:
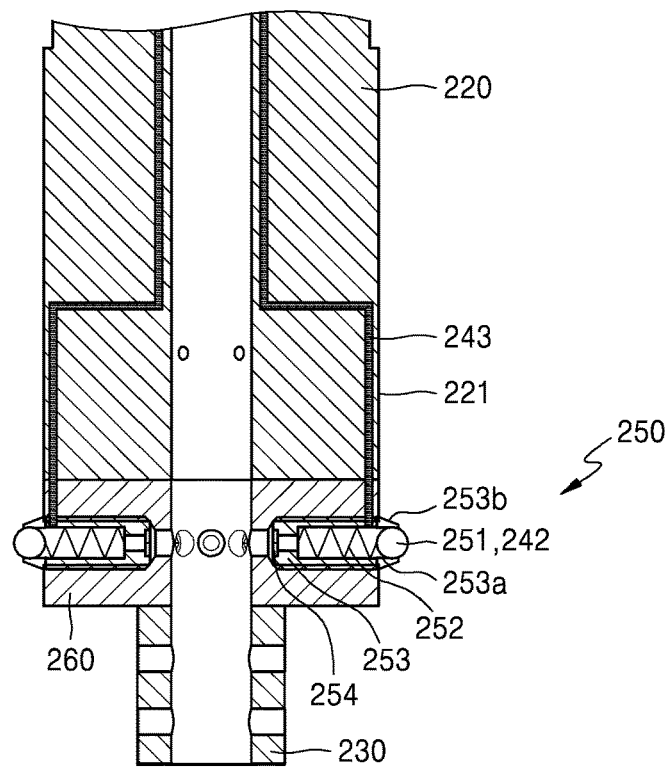
FIG. 4B is a cross-sectional view of part of the transporting rod illustrated in FIG. 4A.
Figure 4C:
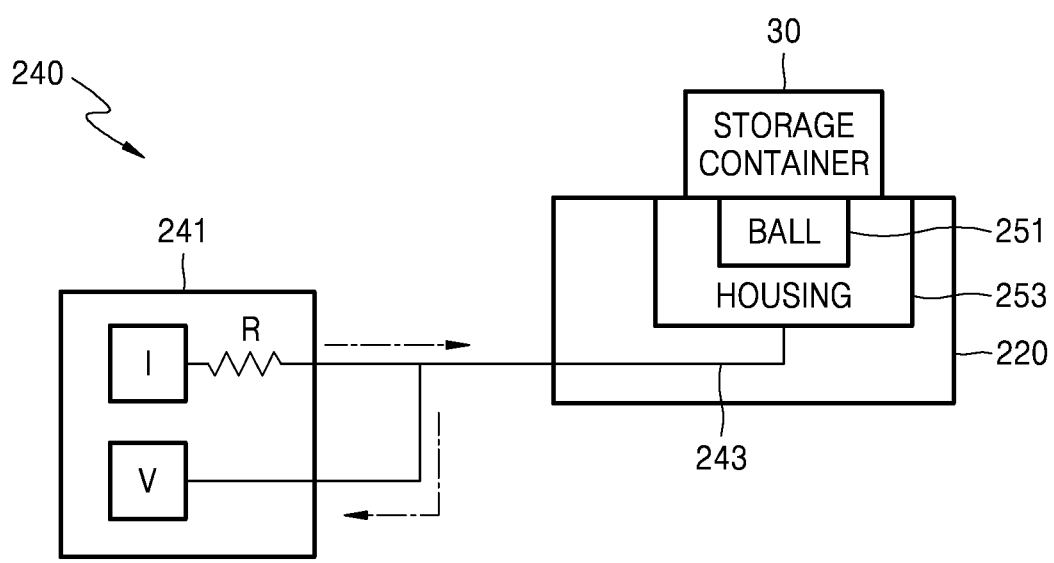
FIG. 4C is a block diagram schematically illustrating a contact sensor portion.

FIG. 4A is a partial perspective view of one end of the transporting rod 200, and FIG. 4B is a cross-sectional view of part of the transporting rod 200 illustrated in FIG. 4A. FIG. 4C is a block diagram schematically illustrating the contact sensor portions 240.

As described above, one or more contact sensor portions 240 may be disposed on one end of the rod portion 220. The one or more contact sensor portions 240 may be implemented as the voltage detection type sensors. The one or more contact sensor portions 240 may include a contact portion 242 that may contact the inner wall portion 32 of the storage container 30 so as to detect contact between the inner wall portion 32 of the storage container 30 and the rod portion 220.

Referring to FIGS. 4A and 4B, for example, balls 251 included in ball plungers 250 may be configured as the contact portion 242 included in the contact sensor portions 240. One or more ball plungers 250 may be disposed on one end of the rod portion 220 in a state in which the ball plungers 250 are disposed around the outer wall portion 221 of the rod portion 220 at intervals separated by a predetermined distance. The ball plungers 250 may include a housing 253, an elastic member 252 that may be compressed or expanded along a lengthwise direction of the housing 253, and the ball 251 which is disposed on one end of the housing 253 and only a part of which may be exposed to an outside of the housing 253.

The housing 253 has a cylindrical shape in which one end of the housing 253 is opened, and is disposed to be fixed to the rod portion 220 using the fastening portion 254 configured of a bolt. A width of an inner wall portion 253a of the housing 253 is formed to be the same as a diameter of the ball 251 so that the ball 251 may be moved along the lengthwise direction of the inner wall portion 253a of the housing 253. An electric wire 243 may be connected to an outer wall portion 253b of the housing 253, and the housing 253 may be formed of a conductor so as to be electrically connected to the detection portion 241 via the electric wire 243.

The elastic member 252 is disposed so that one end of the elastic member 252 may be fixed to one closed end of the housing 253. The elastic member 252 may be disposed in an expanded state to be in contact with the ball 251 disposed on one opened end of the housing 253. When an external pressure is applied to the ball 251, the elastic member 252 may be maintained to be in contact with the ball 251 and may be contracted.

When no external pressure is applied to the ball 251, the ball 251 may be disposed to protrude from the outer wall portion 221 of the rod portion 220 in the lengthwise direction of the housing 253. When the external pressure is applied to the ball 251, the ball 251 may be moved along an inner wall surface of the housing 253 in the lengthwise direction of the housing 253. In this case, the ball 251 may be maintained to be in contact with the housing 253 in which the electric wire 243 is disposed, and may be electrically connected to the detection portion 241 via the electric wire 243 connected to the outer wall portion 253b of the housing 253.

The rod portion 220 further includes an insulation portion 260 that is an insulator disposed between one or more ball plungers 250 and is formed of an insulating material that may prevent electrical connection. The one or more ball plungers 250 may be disposed at regular intervals so as to detect contact with the storage container 30 that may occur in several positions of the rod portion 220. In this case, the insulation portion 260 may be disposed between the ball plungers 250 and may electrically insulate the ball plungers 250 so that electrical connection that may occur between the ball plungers 250 may be prevented.

Referring to FIG. 4C, one or more contact sensor portions 240 may include a detection portion 241 including an input channel I through which reference signals are applied, a receiving channel V through which the reference signals are received, and a resistor R. Through the input channel I, the reference signals, for example, currents, are supplied, the currents supplied by the input channel I pass through the resistor R, and a first reference signal in which a change in voltage occurs is received by the receiving channel V. In this case, the input channel I through which the reference signals are applied, and the receiving channel V through which the first reference signal in which the change in voltage occurs is received, may be electrically connected to the balls 251 of the ball plungers 250 using the electric wire 243. Thus, when the balls 251 are in contact with an external conductor, for example, the storage container 30, through the receiving channel V, a second reference signal having magnitudes of voltages which are changed by contact with the external conductor and which may be different from each other, may be detected. Thus, it may be detected whether the balls 251 of the ball plungers 250 are in contact with the inner wall portion 32 of the storage container 30.

One or more contact sensor portions 240 may be electrically connected to one or more ball plungers 250 via a plurality of electric wires 243. Thus, when one contact portion 242 of one or more contact sensor portions 240 is in contact with the inner wall portion 32 of the storage container 30, voltages detected by the contact sensor portions 240 that are in contact with the inner wall portion 32 of the storage container 30 are changed so that the contact sensor portions 240 in contact with the inner wall portion 32 of the storage container 30 may be discriminated. Thus, a contact position of the transporting rod 200 inserted into the storage container 30 and the storage container 30 may be identified without needing to identify the position and state of the transporting rod 200 by the naked eye.

In the present exemplary embodiment, the balls 251 included in the ball plungers 250 are illustrated as the contact portion 242. However, exemplary embodiments are not limited thereto. The contact portion 242 may be disposed at the outer wall portion 221 of the rod portion 220 and may be in contact with the inner wall portion 32 of the storage container 30. When the contact portion 242 is electrically connected to the detection portion 241 via the electric wire 243, the contact portion 242 may be formed to have an arbitrary shape and an arbitrary structure.

Figure 5A:
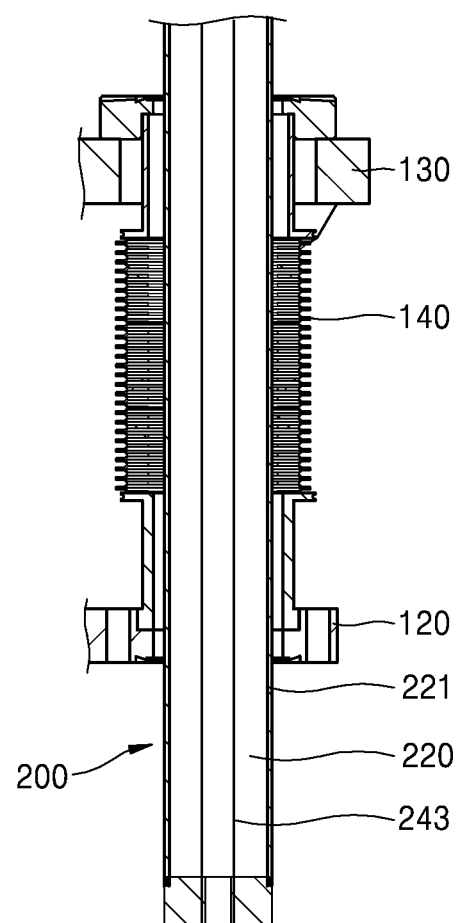
FIG. 5A is a partial cross-sectional view of the transporting apparatus in a state before a rod portion of the transporting apparatus is inserted into the storage container.
Figure 5A:
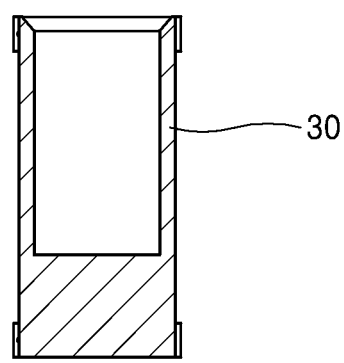
Figure 5B:
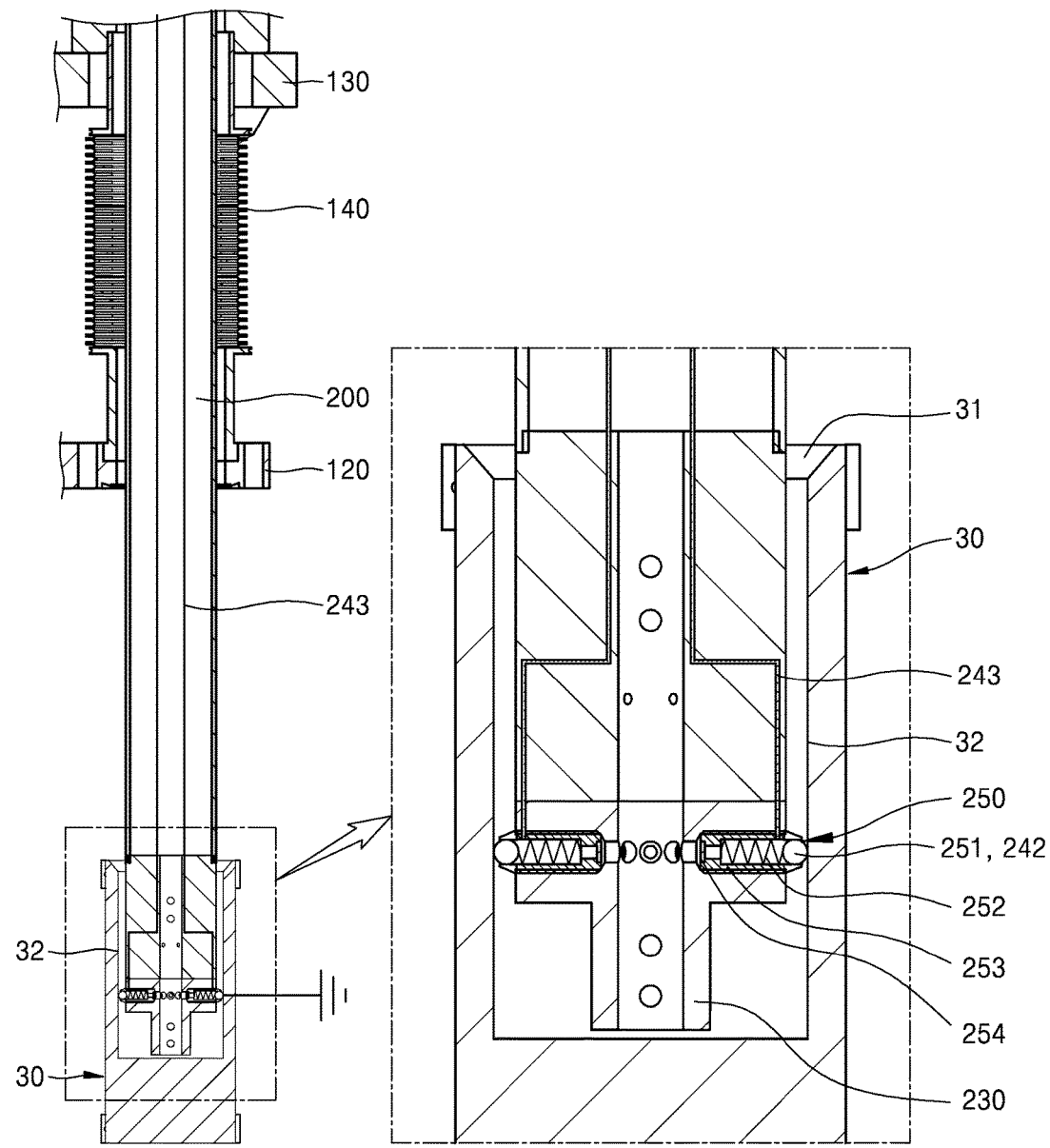
FIG. 5B is a partial cross-sectional view of the transporting apparatus in a state in which the rod portion of the transporting apparatus is inserted into the storage container.

FIG. 5A is a partial cross-sectional view of the transporting apparatus in a state before the rod portion 220 of the transporting apparatus 10 is inserted into the storage container 30, and FIG. 5B is a partial cross-sectional view of the transporting apparatus 10 in a state in which the rod portion 220 of the transporting apparatus 10 is inserted into the storage container 30.

Referring to FIGS. 4C and 5A, when the transporting rod 200 is not inserted into the storage container 30, the balls 251 of the ball plungers 250 are not in contact with the inner wall portion 32 of the storage container 30 and thus the balls 251 protrude from the outer wall portion 221 of the rod portion 220. As described above, the balls 251 of the ball plungers 250 may be used as the contact portion 242 included in one or more contact sensor portions 240. Thus, the first reference signal having a uniform voltage change may be measured through the receiving channel V.

Referring to FIGS. 3, 4C, and 5B, as power generated by the driving portion 150 is transferred to the transporting member 130 using the power transmission portion 145, the transporting member 130 disposed in the transporting portion 100 may be moved downward. In this case, the transporting rod 200 fixed to the transporting member 130 may also be moved in the same direction as that of the transporting member 130, and a movement direction of the transporting rod 200 may be guided by the guide member 120.

As the transporting rod 200 is moved downward, one end of the rod portion 220 is inserted into the opening of the storage container 30. In this case, as the rod portion 220 is inserted into the storage container 30 and moved, the inner wall portion 32 of the storage container 30 and the outer wall portion of the rod portion 220 may be in contact with each other. Thus, the balls 251 of the ball plungers 250 that protrude from the outer wall portion 221 of the rod portion 220 may be in contact with the inner wall portion 32 of the storage container 30. In this case, pressure is applied to the balls 251, thereby moving the balls 251 to an inside of the housing 253. As the balls 251 are moved to the inside of the housing 253, the elastic member 252 may also be compressed.

When the balls 251 are in contact with the inner wall portion 32 of the storage container 30, the second reference signals may be received through the receiving channel V, where the second reference signals have magnitudes of voltages which are changed by contact with the external conductor and which may be different from each other. For example, the inner wall portion 32 of the storage container 30 may be in a grounded state. As the balls 251 of the ball plungers 250 are in contact with the inner wall portion 32 of the storage container 30, a voltage of 0 V may be detected through the receiving channel V. When the second reference signal having a magnitude of voltage which is changed by contact with the external conductor is detected through the receiving channel V, the detected signal may be transmitted to the receiving portion 190. The receiving portion 190 may transmit the received signal to the display portion 180 and the received signal may be displayed on the display portion 180 so that a user may check whether the rod portion 220 is in contact with the storage container 30. Thus, the user may determine whether the transporting rod 200 and the storage container 30 are in contact with each other, while the transporting rod 200 transports the object to be transported from a specimen container that may be used in a semiconductor fabrication process device, a storage container formed of a nontransparent material, or a storage container for a low temperature operation device, for example, a cryogenic scanning probe microscope, through which a movement state of the transporting rod 200 may not easily be checked by the naked eye.

Figure 6:
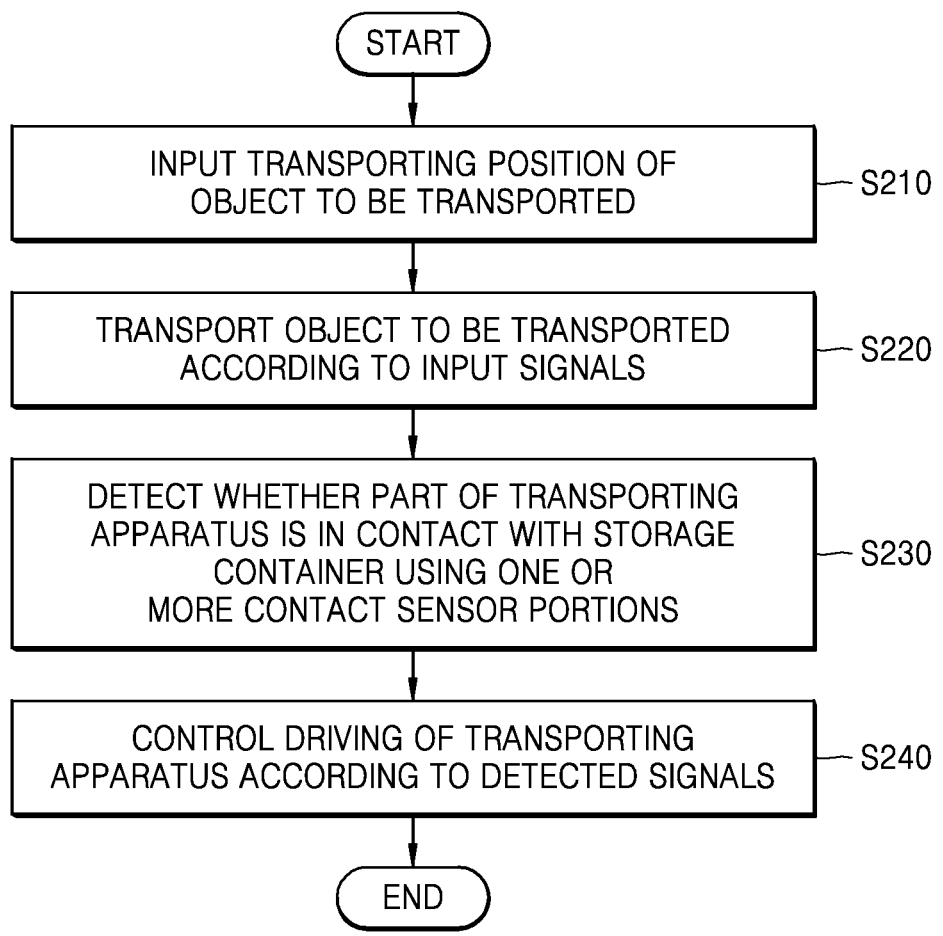
FIGS. 6 and 7 are flowcharts schematically illustrating a method of operating the transporting apparatus, according to an exemplary embodiment.
Figure 7:
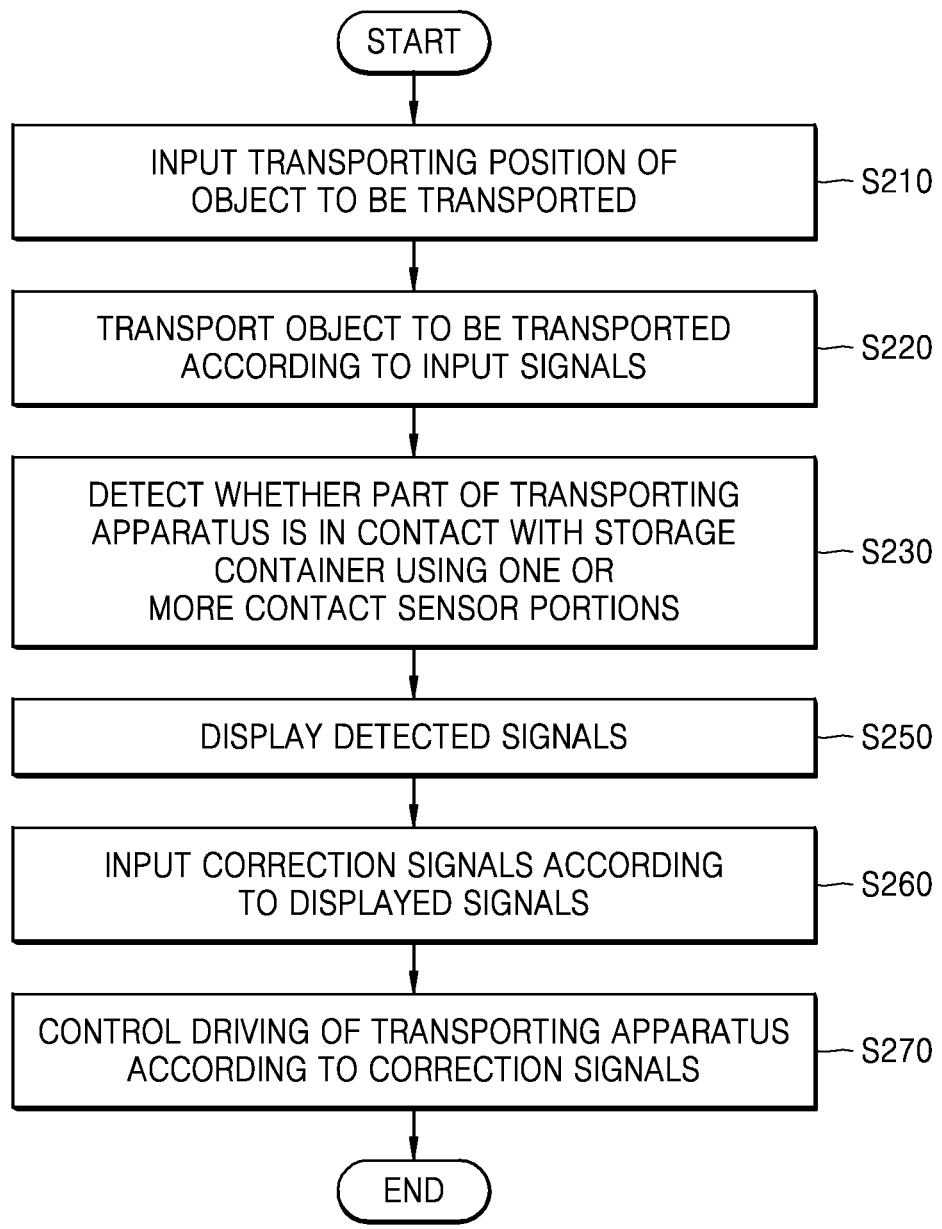

FIGS. 6 and 7 are flowcharts schematically illustrating a method of operating the transporting apparatus, according to an exemplary embodiment. Referring to FIGS. 3, 6, and 7, in operation S210, a signal indicating a transporting position of an object to be transported is input. For example, a position and a direction in which the object to be transported is to be transported, may be input.

Next, in operation S220, the transporting apparatus 10 may transport the object to be transported according to the input signal of operation S210. For example, a value input in the inputting operation of operation S210 may be transferred to the controller 160, and driving signals may be applied to the driving portion 150 based on the value.

The contact sensor portions 240 detect whether part of the transporting apparatus 10, for example, the transporting rod 200, is in contact with part of the storage container 30 in operation S230.

The signals detected by the contact sensor portion 240 may be transmitted to the controller 160. The controller 160 may control the driving of the transporting apparatus 10 according to the received signals and may apply driving signals to the driving portion 150 at operation S240.

Also, as shown in FIG. 7, the detected signals detected by the contact sensor portions 240 in operation S230 are transmitted to the display portion 180, and a contact is displayed on the display portion 180 at operation S250.

It may be determined whether correction of driving of the transporting apparatus 10 is required according to the signals displayed on the display portion 180, and if correction is required, correction signals may be transmitted to the controller 160 at operation S260.

The controller 160 may determine whether the transporting apparatus 10 is driven according to the correction signals and may apply driving signals to the driving portion 150 at operation S270.

As described above, according to the one or more of the above exemplary embodiments, it may be determined whether part of the transporting apparatus is in contact with the storage container while the object to be transported is transported to the storage container even though a user may not be able to identify whether contact is occurring by the naked eye.

Thus, errors may be prevented from occurring due to contact of a transporting apparatus that may be generated while a specimen is transported using a precision device, such as a sample plunger of a cryogenic scanning microscope in which errors may occur in a system even due to fine contact.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A transporting apparatus configured to transport an object to a storage container, the transporting apparatus comprising:
a transporting rod having one end configured to connect to the object, the transporting rod extending in a transporting direction of the object;
a transporting portion that moves the transporting rod in the transporting direction of the object; and
a contact sensor provided on an outer wall of the transporting rod and configured to sense contact with an inner wall of the storage container,
wherein the contact sensor is one of contact sensors provided plurally along a circumferential direction of the transporting rod on the outer wall of the transporting rod at intervals separated by a predetermined distance,
wherein the contact sensors respectively comprise:
contact portions provided on the outer wall of the transporting rod at intervals separated by a predetermined distance,
an input channel electrically connected to the contact portions and configured to detect first reference signals,
a receiving channel electrically connected to the contact portions and the input channel and configured to detect second reference signals in which a change in voltage from the first reference signals occurs,
ball plungers provided along the outer wall of the transporting rod at intervals separated by a predetermined distance, and
balls provided in the ball plungers so that part of the balls is exposed to the outer wall of the transporting rod.

2. The transporting apparatus of claim 1, wherein the transporting apparatus is configured to transport the object to the storage container which is a sealed container.

3. The transporting apparatus of claim 1, wherein the ball plungers are electrically connected to the contact sensors, and the contact portions of the contact sensors are provided on the ball plungers.

4. The transporting apparatus of claim 3, further comprising an insulation member provided between the balls disposed in the ball plungers and formed of an insulating material.

5. The transporting apparatus of claim 1, wherein the transporting apparatus is a sample plunger of a cryogenic scanning probe microscope.

6. The transporting apparatus of claim 1, further comprising:
a transfer holder that is provided on the one end of the transporting rod and configured to grasp the object; and
a transfer holder connector connecting the transfer holder to the one end of the transporting rod.

7. The transporting apparatus of claim 1, further comprising:
a receiving portion configured to receive signals detected by the contact sensor; and
a display configured to display information indicating whether the transporting rod is in contact with the storage container according to the signals received by the receiving portion.

8. The transporting apparatus of claim 7, further comprising:
- an input portion configured to receive driving signals to drive the transporting portion; and
- a controller configured to determine whether to drive the transporting portion according to the signals received by the receiving portion and the driving signals received by the input portion.

9. The transporting apparatus of claim 1, wherein the transporting portion comprises:
- a transporting member fixed to another end of the transporting rod and configured to move in the transporting direction of the object; and
- a guide member provided to face the transporting member and configured as a hollow type plate member configured to receive and guide the transporting rod.

10. The transporting apparatus of claim 9, further comprising a bellows provided between the transporting member and the guide member.

11. A method for transporting an object using a transporting apparatus comprising a contact sensor configured to sense contact between the transporting apparatus and a storage container, the method comprising:
- inputting a transporting position of the object to the transporting apparatus;
- transporting the object to the storage container using the transporting apparatus according to the transporting position;
- detecting whether the contact sensor is in contact with an inner wall of the storage container, by using the contact sensor, and generating a detection signal based on the detecting; and
- controlling driving of the transporting apparatus, according to the detection signal wherein the contact sensor is one of contact sensors provided plurally along a circumferential direction of a transporting rod of the transporting apparatus on an outer wall of the transporting rod at intervals separated by a predetermined distance, wherein the contact sensors respectively comprise:
- contact portions provided on the outer wall of the transporting rod at intervals separated by a predetermined distance,
- an input channel electrically connected to the contact portions and configured to detect first reference signals,
- a receiving channel electrically connected to the contact portions and the input channel and configured to detect second reference signals in which a change in voltage from the first reference signals occurs,
- ball plungers provided along the outer wall of the transporting rod intervals separated by a predetermined distance, and
- balls provided in the ball plungers so that part of the balls is exposed to the outer wall of the transporting rod.

12. The method of claim 11, further comprising:

displaying the detection signal on a display; and inputting correction signals for driving the transporting apparatus according to the detection signal.

* * * * *